United States Patent
Gangjee et al.

(10) Patent No.: US 9,481,678 B2
(45) Date of Patent: Nov. 1, 2016

(54) SUBSTITUTED PYRROLO[2,3-D]DIPYRIMIDINES FOR SELECTIVELY TARGETING TUMOR CELLS WITH FR-ALPHA AND FR-BETA TYPE RECEPTORS

(71) Applicant: DUQUESNE UNIVERSITY OF THE HOLY GHOST, Pittsburgh, PA (US)

(72) Inventors: Aleem Gangjee, Allison Park, PA (US); Larry H. Matherly, Novi, MI (US)

(73) Assignees: Duquesne University of the Holy Ghost, Pittsburgh, PA (US); Wayne State University, Detroit, MI (US)

( * ) Notice: Subject to any disclaimer, the term of this patent is extended or adjusted under 35 U.S.C. 154(b) by 0 days.

(21) Appl. No.: 14/617,332

(22) Filed: Feb. 9, 2015

(65) Prior Publication Data

US 2016/0229857 A1    Aug. 11, 2016

(51) Int. Cl.
*C07D 487/00* (2006.01)
*C07D 487/04* (2006.01)

(52) U.S. Cl.
CPC .................. *C07D 487/04* (2013.01)

(58) Field of Classification Search
None
See application file for complete search history.

(56) References Cited

U.S. PATENT DOCUMENTS

| 5,939,420 A | 8/1999 | Gangjee |
| 2010/0081676 A1 | 4/2010 | Gangjee et al. |
| 2011/0172254 A1 | 7/2011 | Leamon et al. |

OTHER PUBLICATIONS

International Searching Authority, International Search Report and the Written Opinion for International Application No. PCT/US16/13514, mailed Mar. 28, 2016.

Wang et al., "Synthesis, biological and antitumor activity of a highly potent 6-substituted pyrrolo[2,3-d]pynmidine thienoyl antifolate inhibitor with proton-coupled folate transporter and folate receptor selectivity over the reduced folate carrier that inhibits B-glycinamide ribonucleotide formyltransferase", NIH Public Access Author Manuscript—J Med Chem. Author manuscript; available in PMC Oct. 27, 2012, pp. 1-33, Published in final edited form as: J Med Chem. Oct. 27, 2011; 54(20): 7150-7164. doi: 10.1021/jm200739e.

Deng et al., "Synthesis and biological activity of a novel series of 6-substituted thieno[2,3-d]pyrimidine antifolate inhibitors of purine biosynthesis with selectivity for high affinity folate receptors over the reduced folate carrier and proton-coupled folate transporter for cellular entry", NIH Public Access Author Manuscript—J Med Chem. Author manuscript; available in PMC Aug. 21, 2009, pp. 1-30, Published in final edited form as: J Med Chem. May 14, 2009; 52(9): 2940-2951. doi: 10.1021/jm8011323.

*Primary Examiner* — Jeffrey H Murray
(74) *Attorney, Agent, or Firm* — Eckert Seamans Cherin & Mellott, LLC; Carol A. Marmo

(57) ABSTRACT

Pyrrolo[2,3-d]pyrimidine derivatives, and pharmaceutical acceptable salts thereof, useful in therapeutically treating patients with cancer are disclosed. These compounds selectively target folate receptors (FR) of cancerous tumor cells and inhibit purine synthesis and hence, DNA synthesis.

2 Claims, 3 Drawing Sheets

Synthesis of composition 1a

Synthesis of composition 1b

SUBSTITUTED PYRROLO[2,3-D]DIPYRIMIDINES FOR SELECTIVELY TARGETING TUMOR CELLS WITH FR-ALPHA AND FR-BETA TYPE RECEPTORS

GOVERNMENT CONTRACT

This invention was supported in part by the National Cancer Institute of the National Institutes of Health of the U.S. Department of Health and Human Services under Contract Nos. 1R01 CA166711 and 1R01 CA152316. The government has certain rights in the invention.

BACKGROUND OF THE INVENTION

1. Field of the Invention

The present invention relates to compounds that are selective chemotherapeutic agents which selectively target folate receptors (FR) of cancerous tumor cells and inhibit purine synthesis and hence, DNA synthesis. Specifically, the present invention relates to fused cyclic pyrimidines, having unique bridge region variations of pyrrolo[2,3-d]pyrimidines that include three and four atom amide and urea and carbamate linkages, which selectively target folate receptors ("FR"), particularly, FR-alpha and FR-beta of cancerous tumor cells. Methods of preparing and using these compounds are also provided.

2. Description of the Prior Art

Cancer chemotherapy agents as taught, for example in U.S. Pat. No. 5,939,420 to Gangjee, do not specifically selectively target cancer tumor cells. However, chemotherapy agents have targeted both normal and tumor cells. This lack of selectivity for tumor cells results in cytotoxicity to the normal cells and is also one of the major causes of chemotherapeutic failure in the treatment of cancer. Further, advanced stage and platinum resistant tumors may be difficult to treat with traditional chemotherapeutic agents such as, but not limited to, carboplatin or paclitaxel (docitaxel). Other documents in this area include J. Med. Chem. 48 (16), 5329-5336, web release date Jul. 9, 2005 "Synthesis of Classical Four-Carbon Bridged 5-Substituted Furo-[2-3-d]-Pyrimidine and 6-Substituted Pyrrolo-[2,3-d]-Pyrimidine Analogues as Antifolates" by A. Gangjee et al.

As is known in the prior art, a type of folate receptors FR, particularly, FR-alpha and FR-beta, is overexpressed on a substantial amount of certain surfaces of a number of cancerous tumors including, but not limited to, ovarian, endometrial, kidney, lung, mesothelioma, breast, and brain tumors.

In most normal tissues, the FR-alpha and FR-beta are not present. In most normal tissues, folic acid is not taken up by normal cells by way of a reduced folate carrier system (RFC). In light of the specificity of the folic acid, conjugates of folic acid have been used in the prior art to selectively deliver toxins, liposomes, imaging and cytotoxic agents to FR-alpha expressing tumors.

However, one of the major limitations of the foregoing, such as cytotoxic-folic acid conjugates, is that this requires cleavage from the folic acid moiety to release the cytotoxic drug. Even more importantly, premature release of the cytotoxic agent during the transport before reaching the tumor destroys selectivity and thereby leads to undesired toxicity in normal cells. This is a very serious detriment scientifically and commercially.

Further, if the folic acid moiety of the cytotoxic-folic acid conjugate is difficult to cleave, then the anti-tumor activity is hindered as a result of the inability or reduced ability to release the cytotoxic agent. Accordingly, treatment of the tumor cells with the cytotoxic agent is either hindered or rendered nil as a result of the difficulty in cleaving the cytotoxic agent moiety from the folic acid-based conjugate.

In spite of the foregoing prior art, however, there remains a very real need for compositions that selectivity target the FR of tumor cells.

An object of this invention is to provide compositions for selectively targeting FR, in particular, FR-alpha and FR-beta, of tumor cells with a cancer-treating agent that inhibits purine synthesis and hence, DNA synthesis.

In a related object, the compound does not contain conjugated compositions and does not need cleavage to release a cytotoxic drug.

In yet another related object, the compound will allow penetration into the cancerous cells expressing FR, that is, FR-alpha and/or FR-beta, but not into a cell using the reduced folate carrier system (RFC).

Another object of this invention is to provide a non-toxic FR targeting compound to the cancerous tumor in the process of treating a patient.

Another object of this invention is to efficiently target a cancerous tumor.

Another object of this invention is to utilize an essentially noncompound useful in treating a cancerous tumor.

SUMMARY OF THE INVENTION

The present invention has filled the above described need and satisfied the above objects by providing a narrow range of compounds that selectively target the FR of tumor cells. The term "FR" used herein includes receptors selected from the group consisting of FR-alpha, FR-beta and mixtures thereof. In a preferred embodiment, the compositions selectively target FR-alpha and beta of cancerous tumor cells.

Very significantly, the cancer-treating compound is not significantly taken up by a cell or tissue using the RFC system.

The cancer-treating agent is a fused cyclic pyrimidine and is used to selectively target FR of tumors, advanced stage cancerous tumors that express FR receptors and drug-resistant tumors such as, but not limited to, those resistant to carboplatin, paclitaxel, and/or docitaxel. The receptors are preferably FR-alpha and -beta types.

More specifically, the invention relates to a compound that is useful in inhibiting purine synthesis and hence, DNA synthesis in a cancerous tumor of a patient consisting essentially of a fused cyclic pyrimidine, where there are unique bridge region variations between the major ring groups; wherein the compound is effective to selectively target a FR cancerous tumor, where the fused cyclic pyrimidine targets primarily cancerous tumors which contain FR to inhibit purine synthesis and hence, DNA synthesis within the tumors.

An aspect of the present invention is to provide pyrrolo[2,3-d]pyrimidine compounds and pharmaceutically acceptable salts thereof, having the formula 1:

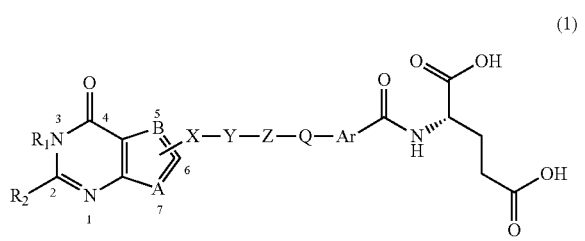

(1)

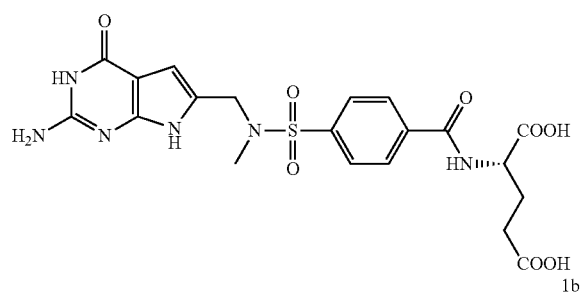

1a

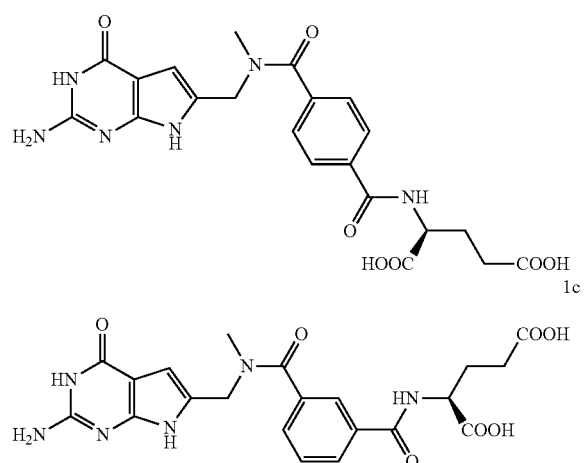

1b

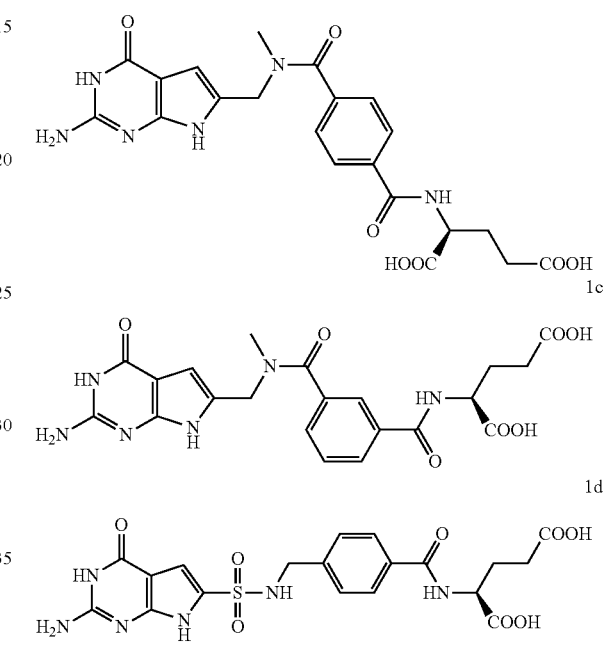

1c

1d wherein, $R_1$ is selected from the group consisting of hydrogen (H), hydroxyl (OH), methyl ($CH_3$) and NHR wherein R is selected from the group consisting of H, lower alkyl, and a tautomer of the hydroxyl or the NHR;

$R_2$ is selected from the group consisting of hydrogen (H), hydroxyl (OH), methyl ($CH_3$) and NHR wherein R is selected from the group consisting of H and lower alkyl;

A is selected from the group consisting of sulfur (S), oxygen (O), CR'R" and NR', wherein R' and R" are the same or different and each is selected from the group consisting of H and lower alkyl;

B is selected from the group consisting of sulfur (S), oxygen (O), CR'R" and NR', wherein R' and R" are the same or different and each is selected from the group consisting of H and lower alkyl;

A and B are the same or different;

the chemical bond between positions 5 and 6 is selected from the group consisting of a single bond and a double bond;

the position of the side chain on the five-membered ring is selected from the group consisting of position 5, 6 and 7;

when the side chain is at position 7, A is selected from the group consisting of CR' and N, and optionally, carbon atoms at positions 5 and 6, independently, have attached thereto a substituent selected from the group consisting of two hydrogen atoms when the bond between the carbon atoms 5 and 6 is a single bond and a hydrogen atom when the bond between the carbon atoms 5 and 6 is a double bond, and a lower alkyl group and a hydrogen atom when the bond between the carbon atoms at positions 5 and 6 is a single bond or a lower alkyl when the bond between the carbon atoms 5 and 6 is a double bond;

each of X, Y, Z and Q is selected from the group consisting of carbonyl, sulfonyl, oxygen, $(CR'R")_n$ and NR', wherein n is 0 to 6, R' and R" are the same or different, and each of R' and R" is selected from the group consisting of hydrogen, straight or branched lower alkyl, partially to fully fluoro substituted alkyl, benzyl, formyl, methylketone, trifluoromethyl ketone;

X, Y, Z and Q are different or two of X, Y, Z and Q are the same;

Ar is selected from the group consisting of phenyl, thiophene, pyridine, naphthyl, indole, benzothiophene, substituted and unsubstituted aromatic, substituted and unsubstituted heteroaromatic and, partially and completely reduced aromatic and heteroaromatic;

when Ar is a six-membered ring and one of X, Y and Z is carbonyl, the Q and carbonyl substituents are meta or para; and when Ar is a five-membered ring and one of X, Y and Z is carbonyl, the Q and carbonyl substituents are in positions selected from the group consisting of 2,4 and 2,5 and 3,5.

In certain embodiments, the formula 1 provides pyrrolo [2,3-d]pyrimidine compounds and pharmaceutically acceptable salts thereof, having the formulas 1a, 1b, 1c and 1d:

In another aspect, the invention provides methods of using the compounds and pharmaceutically acceptable salts thereof for therapeutic purposes as antitumor agents or to otherwise destroy cancer cells in cancer patients, described herein.

It is an object of this invention to provide pyrimidine derivative compounds, and pharmaceutically acceptable salts thereof, for substantially inhibiting purine synthesis and hence, DNA synthesis.

It is another object of this invention to provide pyrimidine derivative compounds, and pharmaceutically acceptable salts thereof, having effective activity against tumors and other cancerous cells, such as those caused by cancer including, but not limited to, ovarian, lung and breast cancers.

It is a further object of this invention to provide methods of administering to a patient a therapeutically effective amount of pyrimidine derivative compounds, or pharmaceutically acceptable salts thereof.

The invention will be more fully understood by review of the drawings in view of the following detailed description of the invention, and the claims appended thereto.

DESCRIPTION OF THE PREFERRED EMBODIMENTS

Figure 1A:
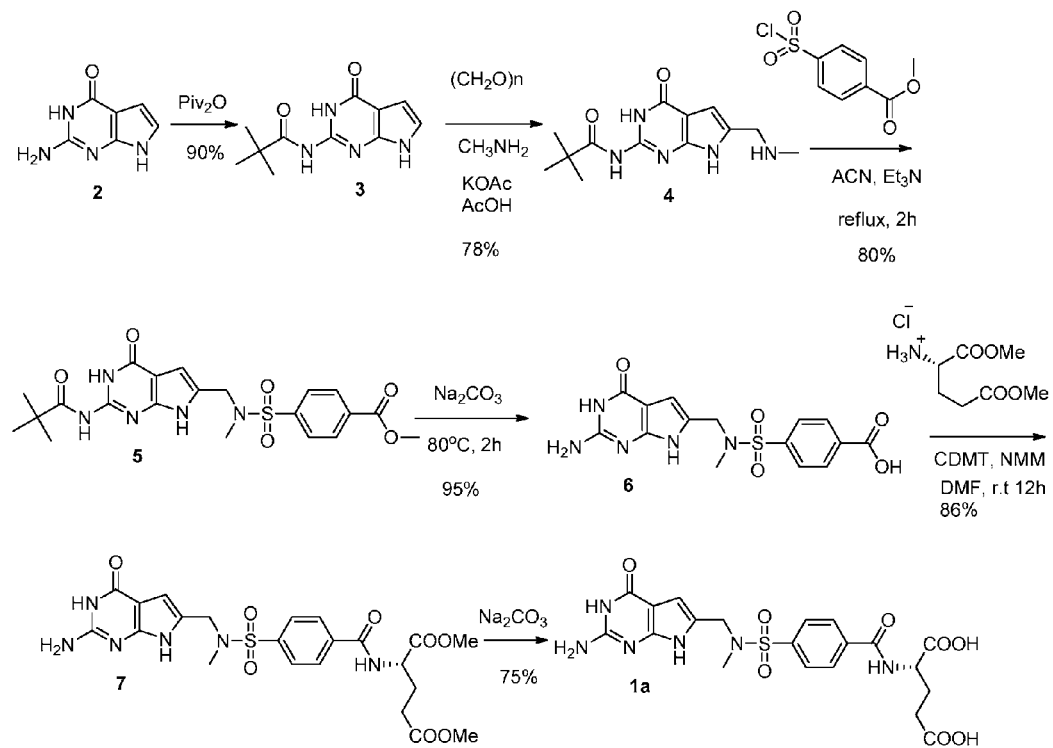
FIG. 1a shows a reaction scheme for synthesis of the pyrrolo[2,3-d]pyrimidine compound of the chemical formula 1a, in accordance with certain embodiments of the invention.

The present invention relates to substituted pyrrolo[2,3-d]pyrimidines for targeting tumor cells with FR-alpha and -beta receptors. These compounds have unique bridge region variations that include three and four atom amide and urea and carbamate linkages that target folate receptor alpha and beta of tumors selectively over the reduced folate carrier (RFC) used by normal cells. Thus, these compounds are FR-alpha and PCFT transport agents without RFC transport activity. The selectivity provides for antitumor activity without toxicity to normal cells and hence, without dose-limiting toxicity (which is associated with other known antitumor agents). These compounds are potent inhibitors of purine synthesis and hence, of DNA synthesis. It has been found that these compounds have antitumor activity against FR-alpha expressing KB tumor cells at $IC_{50}$ 0.29 nM and the pteroic acid precursor has $IC_{50}$ equal to 22.22 µM against KB tumors. These are unexpected findings for these compounds. Without being bound by any particular theory, it is believed that the unexpected results relate to the unique bridge region variations and use of pteroic acid. The pteroic acid analog has excellent antitumor activity.

As used herein, "tumor" refers to an abnormal growth of cells or tissues of the malignant type, unless otherwise specifically indicated and does not include a benign type tissue. The "tumor" may comprise of at least one cell and/or tissue. The term "inhibits or inhibiting" as used herein means reducing growth/replication. As used herein, the term "cancer" refers to any type of cancer, including ovarian cancer, leukemia, lung cancer, colon cancer, CNS cancer, melanoma, renal cancer, prostate cancer, breast cancer, and the like. As used herein, the term "patient" refers to members of the animal kingdom including but not limited to human beings.

As used herein, the term "pharmaceutically acceptable salts" includes, but is not limited to, acetate, formate, glucuronate, ethanate, sulfonate, or other salts known to those skilled in the art. As used herein, the term "$C_1$-$C_6$ alkyl" refers to an alkyl group having between 1 and 6 carbons.

The fused cyclic pyrimidine compounds and pharmaceutically acceptable salts thereof, and method of preparing and using the compounds of this invention, provide for the therapeutic treatment of tumors or other cancer cells in cancer patients.

The compounds disclosed in the present invention all can be generally described as antifolates.

The fused cyclic pyrimidine of the invention has six unique properties: 1) inhibition of FR-alpha and beta cancerous tumors, 2) a lack of appreciable uptake by the RFC; 3) ability to act itself as a cancer treating agent; 4) ability to penetrate cancerous tumors having folate receptors; 5) ability to function as a substrate of folylpolyglutamate synthetase (FPGS) thereby being trapped in tumor cells; and 6) inhibition of purine synthesis and hence, DNA synthesis. The fused cyclic pyrimidine of this invention targets cancers with certain receptors, and is practically non-toxic. These fused cyclic pyrimidines are taken into the tumor cells.

Selectivity of the fused cyclic pyrimidine is made possible since most normal cells do not have FRs. FR-alpha is the most widely expressed receptor isoform in adult tissue. FR-alpha occurs at the apical (i.e., luminal) surface of epithelial cells where it is not supplied by folate in the circulation and does not take it up into the cell.

The pyrrolo[2,3-d]pyrimidine compounds, and pharmaceutically acceptable salts thereof, of the present invention have the general formula 1:

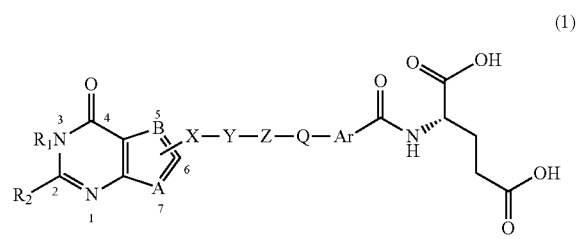

(1)

wherein, $R_1$ is selected from the group consisting of hydrogen (H), hydroxyl (OH), methyl ($CH_3$) and NHR wherein R is selected from the group consisting of H, lower alkyl, and a tautomer of the hydroxyl or the NHR;

$R_2$ is selected from the group consisting of hydrogen (H), hydroxyl (OH), methyl ($CH_3$) and NHR wherein R is selected from the group consisting of H and lower alkyl;

A is selected from the group consisting of sulfur (S), oxygen (O), CR'R" and NR', wherein R' and R" are the same or different and each is selected from the group consisting of H and lower alkyl;

B is selected from the group consisting of sulfur (S), oxygen (O), CR'R" and NR', wherein R' and R" are the same or different and each is selected from the group consisting of H and lower alkyl;

A and B are the same or different;

the chemical bond between positions 5 and 6 is selected from the group consisting of a single bond and a double bond;

the position of the side chain on the five-membered ring is selected from the group consisting of position 5, 6 and 7;

when the side chain is at position 7, A is selected from the group consisting of CR' and N, and optionally, carbon atoms at positions 5 and 6, independently, have attached thereto a substituent selected from the group consisting of two hydrogen atoms when the bond between the carbon atoms 5 and 6 is a single bond and a hydrogen atom when the bond between the carbon atoms 5 and 6 is a double bone, and a lower alkyl group and a hydrogen atom when the bond between the carbon atoms at positions 5 and 6 is a single bond or a lower alkyl when the bond between the carbon atoms 5 and 6 is a double bond;

each of X, Y, Z and Q is selected from the group consisting of carbonyl, sulfonyl, oxygen, (CR'R")$_n$ and NR', wherein n is 0 to 6, R' and R" are the same or different, and each or R' and R" is selected from the group consisting of hydrogen, straight or branched lower alkyl, partially to fully fluoro substituted alkyl, benzyl, formyl, methylketone, trifluoromethyl ketone;

X, Y, Z and Q are different or two of X, Y, Z and Q are the same;

Ar is selected from the group consisting of phenyl, thiophene, pyridine, naphthyl, indole, benzothiophene, substituted and unsubstituted aromatic, substituted and unsubstituted heteroaromatic and, partially and completely reduced aromatic and heteroaromatic;

when Ar is a six-membered ring and one of X, Y and Z is carbonyl, the Q and carbonyl substituents are meta or para; and when Ar is a five-membered ring and one of X, Y and Z is carbonyl, the Q and carbonyl substituents are in a position selected from the group consisting of 2,4 and 2,5 and 3,5.

In certain embodiments, the formula 1 provides pyrrolo[2,3-d]pyrimidine compounds and pharmaceutically acceptable salts thereof, having the formulas 1a, 1b, 1c and 1d:

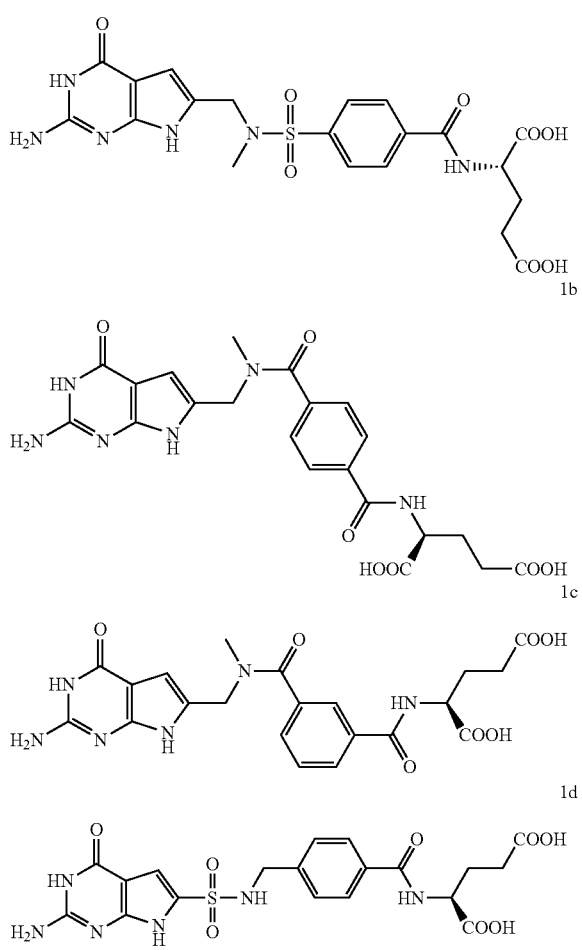

As used herein, the term "lower alkyl" group refers to those lower alkyl groups having one to about six carbon atoms, such as for example methyl, ethyl, propyl, butyl, pentyl, hexyl, cyclopropyl, cyclobutyl, cyclohexyl, cyclopropylmethyl, or cyclobutylmethyl groups. Alkyl groups sharing one to about six carbon atoms are preferred. These lower alkyl groups may be straight chain, branched chain, or cyclic (alicyclic hydrocarbon) arrangements. The carbon atoms of these straight chain, branched chain, or cyclic arranged alkyl groups may have one or more substituents for the hydrogens attached to the carbon atoms.

Figure 1B:
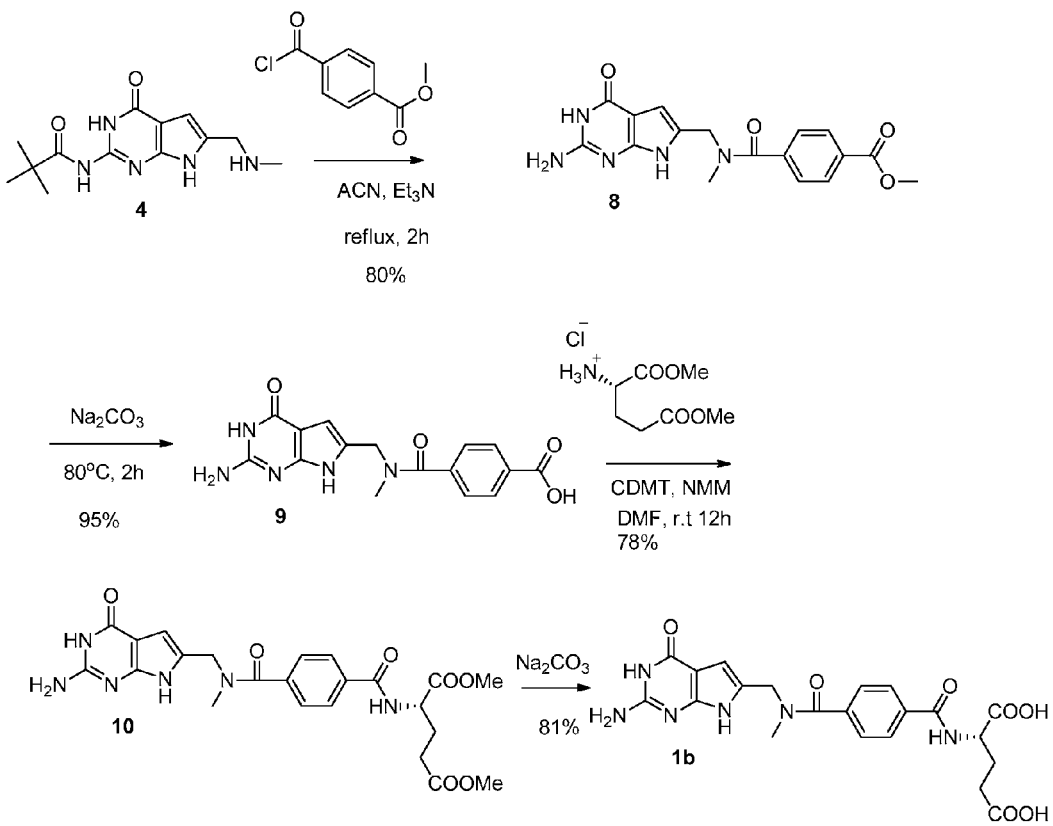
FIG. 1b shows a reaction scheme for synthesis of the pyrrolo[2,3-d]pyrimidine compound of the chemical formula 1b, in accordance with certain embodiments of the invention.
Figure 1C:
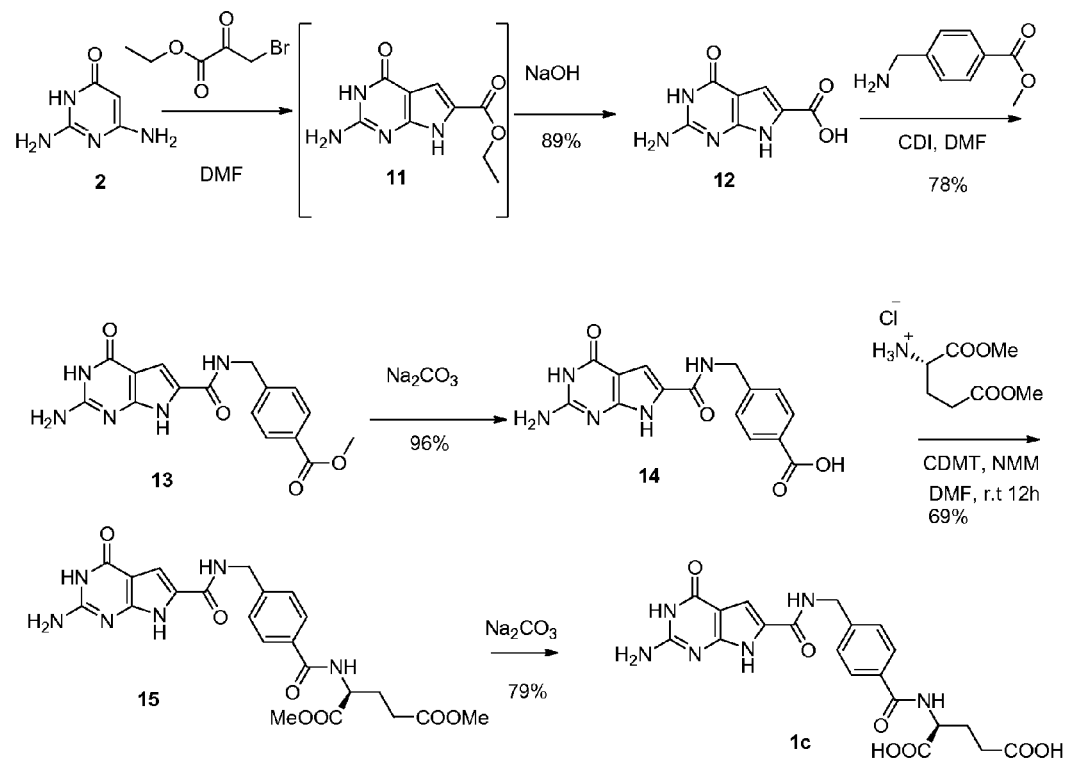
FIG. 1c shows a reaction scheme for synthesis of the pyrrolo[2,3-d]pyrimidine compound of the chemical formula 1c, in accordance with certain embodiments of the invention.

FIGS. 1a, 1b and 1c show reaction schemes for synthesis of the pyrrolo[2,3-d]pyrimidine compounds of the chemical formula 1a, 1b and 1c, in accordance with certain embodiments of the invention.

The present invention further relates to methods of using the above-described compounds, and pharmaceutically acceptable salts thereof, in treating patients with cancer. A method of therapeutically treating a patient for cancer includes the steps of:

a) employing a compound, or pharmaceutically acceptable salts thereof, having the above general formula 1;

b) incorporating said compound in a suitable pharmaceutical carrier; and c) administering a therapeutically effective amount of said compound incorporated in said carrier to a patient.

As used herein, the term "therapeutically effective carrier" refers to any pharmaceutical carrier known in the art to solubilize the present compounds and will not give rise to compatibility problems with the compounds of formula 1, and includes any and all solvents, dispersion media and the like. Preferred carriers include physiologic saline and 5% dextrose.

As will be understood by one skilled in the art, a therapeutically effective amount of said compound can be administered to a patient by any means known in the art, including but not limited to, injection, parenterally and orally.

It is well within the skill of one practicing in the art to determine what dosage, and the frequency of this dosage, which will constitute a therapeutically effective amount for each individual patient, depending on the severity or progression of cancer or cancer cells and/or the type of cancer. It is especially advantageous to formulate compositions in dosage unit form for ease of administration and uniformity of dosage. Dosage unit form as used herein refers to physically discrete units suited as unitary dosages for the patients being treated, each unit containing a predetermined quantity or effective amount of pyrrolo[2,3-d]pyrimidine compound to produce the desired effect in association with the therapeutically effective carrier. The specification for the dosage unit forms of the invention are dictated by and directly dependent on the particular compound and the particular effect to be achieved. It is also within the skill of one practicing in the art to select the most appropriate method of administering the compounds based upon the needs of each patient.

The fused cyclic pyrimidine has a particular affinity for the receptors such as FR or FR-alpha or FR-beta which are mainly present on the surface of cancerous tumor cells and are not present on other types of folate transport systems that are more predominant on the surface of normal cells. In other words, the fused cyclic pyrimidine of this invention, preferably is not taken up to an appreciable degree by the reduce folate carrier (RFC) system. FR-alpha and beta receptors are generally not expressed in normal cells. The fused cyclic pyrimidine stays inside of the cancerous tumor cell for an adequate amount of time to kill the tumor cell. This occurs by way of polyglutamylation and the multi-ionic form of the fused cyclic pyrimidine itself inside of the tumor cell. The fused cyclic pyrimidine also disrupts the replication process of the cancerous tumor cell, thereby inhibiting the growth of FR-alpha expressing cancerous tumor cells.

The foregoing embodiments are enabled by way of purine synthesis inhibition, which is essential to DNA synthesis of normal and cancerous tumor cells.

The fused cyclic pyrimidine itself has a high affinity for the FR-alpha and FR-beta receptors which are overexpressed on the surface of cancerous tumor cells. The fused cyclic pyrimidine passing into the cancerous tumor cells inhibits purine synthesis and hence, inhibits DNA synthesis. Accordingly, the targeted tumor cells which overexpress FR-alpha and FR-beta are prevented from replicating and are killed.

In a preferred embodiment, the fused cyclic pyrimidine has a significantly greater affinity for FR-alpha and FR-beta expressing cells (i.e., certain cancerous tumor cells as described in more detail above) compared with cells that do not express FR-alpha or FR-beta.

At present, there appears to be no other agents known with the above-described six attributes in a single chemotherapy agent and therefore the presently invented compositions are unique with regard to other purine inhibiting or FR-alpha and FR-beta targeting agents, including any known agent in clinical or investigational use.

Compounds that are covered under formula 1 may also be administered with one or more additional treatment agents, e.g., a chemotherapeutic agent. Suitable candidates for the additional chemotherapeutic agent include but are not limited to paclitaxel, docetaxel, vinca alkaloids, colchicine, colcemid, cisplatin, and nocadazol. The present of the pyrrolo[2,3-d]pyrimidine compounds will enhance the effectiveness of the chemotherapeutic agent. In certain embodiments, compounds having formula (1) may be combined with the additional chemotherapeutic agents and administered together, either in the same pharmaceutical carrier, or in different carriers but at generally the same time. In another embodiment, compounds having formula (1) may be administered prior to and separately from the additional chemotherapeutic agents, giving the pyrrolo[2,3-d]pyrimidine compound. The administration of a compound having formula (1) along with an additional chemotherapeutic agent may result in a synergistic effect. Synergism occurs when two compounds used together have a great effect than when the two compounds are used separately. When synergism occurs, it is possible to use less of each compound.

Moreover, other embodiments of the invention will be apparent to those skilled in the art from consideration of the specification and practice of the invention disclosed herein. It is intended that the specification be considered as exemplary only. Furthermore, the following examples are meant to be illustrative of certain embodiments of the invention and are not intended to be limiting as to the scope of the invention.

EXAMPLES

Scheme 1 Synthesis of Compound 1a (as Shown in FIG. 1a)

2-Pivaloylamino-4-hydroxy-pyrrolol[2,3-d]pyrimidine (compound 3)

2-Amino-4-hydroxy-pyrrolol[2,3-d]pyrimidine (compound 2) (15 g, 100 mmol) and pivalic anhydride 50 mL were combined and stirred at 120° C. for 4 hours. The solvent in the reaction mixture was removed under high vacuum to give a dark solid. The resultant residue was washed with 500 mL dry acetone and filtered to give a pale power 42.1 g (90% yield), $R_f$0.60 ($CHCl_3/CH_3OH$, 10/1); $^1H$ NMR (DMSO-$d_6$) δ 1.25 (s, 9H) 6.02 (d, 1H), 6.98 (d, 1H), 8.93 (br, 1H-ex), 10.60 (br, 1H), 11.22 (br, 1H).

6-Methylaminomethyl Pyrrolo[2,3-d]pyrimidine (compound 4)

Methyl amine (0.34 g, 11 mmol) and paraformaldehyde (0.33 g, 1.1 mmol) in 5 mL AcOH were combined and stirred at 50° C. for 3 hours. After all the paraformaldehyde was completely dissolved, compound 3 (2.34 g, 10 mmol) was added to the above solution and stirred at room temperature for another 12 hours. The solvent was removed, and silica gel plaque was made. Column separation offered a purified light yellow solid 2.16 g compound 4 in 78% yields. $R_f$0.10 ($CHCl_3/CH_3OH$, 10/1); $^1H$ NMR (DMSO-$d_6$) δ 1.24 (s, 9H) 2.62 (s, 3H), 3.90 (d, 2H), 6.04 (d, 1H), 8.82 (br, 1H), 10.63 (br, 1H), 11.21 (br, 1H).

Methyl 4-[4-(2-Amino-4-oxo-4,7-dihydro-3H-pyrrolo[2,3-d]-pyrimidin-6-yl)-N-methyl-methylaminosulfonyl]phenyl-4-carboxylate (compound 5)

Compound 4 (2.77 g, 10 mmol) and methyl-4-chlorosulfonylbenzenecarboxylate (2.46 g, 10.5 mmol) were dissolved in 30 mL DMF. TEA (3.03 g, 3 eq) was added and the solution was stirred for 12 hours at room temperature. The solvent was removed and silica gel plaque was made. Column separation offered a purified white powder compound 5 in 80% yields, $R_f$0.25 ($CHCl_3/CH_3OH$, 10/1); $^1H$ NMR (DMSO-$d_6$) δ 1.26 (s, 9H), 2.60 (2, 3H), 4.21 (s, 2H, 6.25 (s, 1H), 7.94 (d, 2H), 8.06 (d, 2H), 10.91 (br, 1H), 11.63 (br, 1H), 11.91 (br, 1H).

4-[4-(2-Amino-4-oxo-4,7dihydro-3H-pyrrolo[2,3-d]-pyrimidin-6-7yl]-N-methyl-methylaminosulfonyl] phenyl-4-carobxylate (compound 6)

Compound 5 (0.475 g, 1 mmol) was dissolved in 10 mL MeOH and 10 mL 3N sodium carbonate, and stirred for 12 hours at room temperature. The solvent was removed, 10 mL water was added and the pH was neutralized to 3-4 by 1N HCl. The solution was filtered and dried to give a white powder. 0.35 g in 95% yields, $R_f$0.10 ($CHCl_3/CH_3OH/AcOH$, 10/1/0.5); $^1H$ NMR (DMSO-$d_6$) δ 2.55 (s, 3H) 4.02 (s, 2H), 6.02 (s, 1H), 6.05 (s, 2H), 7.75 (d, 2H), 8.12 (d, 2H), 10.40 (br, 1H), 11.03 (br, 1H), 12.30 (br, 1H).

2-({4-[4-(2-Amino-4-oxo-4,7-dihydro-3H-pyrorolo[2,3-d]-pyrimidin-6-yl))-N-methyl-methylaminosulfonyl]phenyl-4-carbonyl}amino)pentanedioic dimethyl ester (compound 7)

To a 250 mL round-bottomed flask was added a mixture of compound 6 (0.301 g, 0.8 mmol), N-methylmorpholine (0.165 g, 1.6 mmol), 2-chloro-4,6-dimethoxy-1,3,5-triazine (0.175 g, 1 mmol), and anhydrous DMF (6 mL). The mixture was stirred for 1.5 hours at room temperature. N-methylmorpholine (0.165, 1.6 mmol) and L-glutamic acid dimethyl ester hydrochloride (0.211 g, 1 mmol) were added to the flask, and the reaction mixture was then stirred at room temperature for 12 hours. After evaporation of solvent under reduced pressure, MeOH (20 mL) was added followed by silica gel (2.5 g). The resulting plug was loaded onto a silica gel column (2.5 cm×12 cm) and eluted with 10% MeOH in $CHCl_3$. Fractions with the desired $R_f$0.41 ($CHCl_3/CH_3OH$, 10/1); $^1H$ NMR (DMSO-$d_6$) 61.90 (m, 2H), 2.32 (m, 2H), 2.64 (s, 3H), 3.78 (d, 6H), 4.24 (s, 2H), 4.61 (m, 1H), 5.89 (s, 2H), 6.14 (s, 1H), 7.89 (d, 2H), 8.03 (br, 1H), 8.22 (d, 2H), 9.90-10.50 (br, 2H).

2-({4-[4-(2-Amino-4-oxo-4,7-dihydro-3H-pyrrolo[2,3-d]pyrimidin-6-yl)-N-methyl-methylaminosulfonyl] phenyl-4-carbonyl}amino)pentanedioic acid (compound 1a)

Compound 7 (2.68 g, 0.5 mmol) was dissolved in 10 mL MeOH and 10 mL 3N sodium carbonate, and stirred for 12 hours at room temperature. The solvent was removed and 10 mL water was added, pH was neutralized to 3-4 by 1N HCl. The solution was filtered and dried to give a white powder 0.18 g in 75% yields. $R_f$ 0.10 ($CHCl_3/CH_3OH/AcOH$, 10/1/0.5); $^1H$ NMR (DMSO-$d_6$) δ 1.92 (m, 1H), 2.08 (m, 1H), 2.40 (m, 2H), 2.55 (s, 3H), 409 (s, 2H), 4.44 (m, 1H), 6.11 (m, 3H), 7.90 (d, 2H), 8.12 (d, 2H), 8.90 (d, 1H), 10.30 (br, 1H), 11.12 (br, 1H), 12.15 (br, 1H), 12.67 (br, 1H). anal. ($C_{20}H_{22}N_6O_8S$. 0.29$H_2O$.0.63AcOH) C HNS.

Scheme 2 Synthesis of Compound 1b (as shown in FIG. 1b)

Methyl 4-[4-(2-Amino-4-oxo-4,7-dihydro-3H-pyrrolo[2,3-d]-pyrimidin-6-yl)-N-methyl-methylaminocarbonyl]phenyl-4-carboxylate (compound 8)

Compound 4 (0.277 g, 1 mmol) and methyl 4-chlorocarbonylbenzencarboxylate (0.208 g, 1.05 mmol) were dissolved in 3 mL DMF. TEA (0.303 g, 3 eq.) was added and stirred for 12 hours at room temperature. All the solvent was removed and directly made silica gel plague. Column separation offered purified white powder 0.350 g compound 8 in 80% yields. $R_f$ 0.15 ($CHCl_3/CH_3OH$, 40/1); $^1H$ NMR (DMSO-$d_6$) δ1.26 (s, 9H), 2.95 (d, 2H), 3.95 (s, 3H), 4.42-4.70 (d, 2H), 6.05-6.09 (d, 1H), 7.60 (d, 2H), 8.03 (d, 2H), 10.60 (br, 1H,), 11.63 (br, 1H), 11.95 (br, 1H).

4-[4-(2-Amino-4-oxo-4,7-dihydro-3H-pyrrolo[2,3-d]-pyrimidin-6-yl)-N-methyl-methylaminocarbonyl]phenyl-4-carboxylate (compound 9)

Compound 8 (0.219, 0.5 mmol) was dissolved in 10 mL MeOH and 10 mL 3N sodium carbonate, and stirred for 12 hours at room temperature. All the solvent was removed, 10 mL of water was added, the pH was neutralized to 3-4 by 1N HCl. Filtered and dried to give white powder 0.162 g in 95% yield. $R_f$ 0.53 ($CHCl_3/CH_3OH/AcOH$, 10/1/0.5); $^1H$ NMR (DMSO-$d_6$) δ 2.80-3.00 (d, 3H), 4.29-4.58 (d, 2H), 6.00 (m, 3H), 7.57 (d, 2H), 7.98 (d, 2H), 10.24 (br, 1H), 11.03 (br, 1H), 13.14 (br, 1H). anal. ($C_{16}H_{15}N_5O_4$. 1.4$H_2O$) CHN.

2-({4-[4-(2-Amino-4-oxo-4,7-dihydro-3H-pyrrolo[2,3-d]-pyrimidin-6-yl))-N-methyl-methylaminocarbonyl]phenyl-4-carbonyl}amino)pentanedioic dimethyl ester (compound 10)

To a 250 mL round-bottomed flask was added a mixture of compound 9 (0.102 g, 0.3 mmol), N-methylmorpholine (0.061 g, 0.6 mmol), 2-chloro-4,6-dimethoxy-1,3,5-triazine (0.07 g, 0.4 mmol), and anhydrous DMF (2 mL). The mixture was stirred for 1.5 hours at room temperature. N-methylmorpholine (0.06 g, 0.6 mmol) and L-glutamic acid dimethyl ester hydrochloride (0.084 g, 0.4 mmol) were added to the flask, and the reaction mixture was then stirred at room temperature for 12 hours. After evaporation of solvent under reduced pressure, MeOH (20 mL) was added followed by silica gel (1 g). The resulting plug was loaded onto a silica gel column (2.5 cm×12 cm) and eluted with 10% MeOH in $CHCl_3$. Fractions with the desired Rf (TLC) were pooled and evaporated to give white powder 0.155 g in 78% yield. $R_f$ 0.23 ($CHCl_3/CH_3OH$, 10/1); $^1H$ NMR (DMSO-$d_6$) δ2.02 (m, 1H), 2.14 (m, 1H), 2.86 (d, 3H), 3.61 (d, 6H), 4.30 (d, 2H), 4.58 (m, 1H), 6.02 (m, 3H), 7.55 (d, 2H), 7.94 (d, 2H), 8.87 (d, 1H), 10.25 (br, 1H), 11.02 (br, 1H).

2-({4-[4-(2-Amino-4-oxo-4,7-dihydro-3H-pyrrolo[2,3-d]-pyrimidin-6-yl))-N-methyl-methylaminocarbonyl]phenyl-4-carbonyl}amino)pentanedioic acid (compound 1b)

Compound 10 (0.099 g, 0.2 mmol) was dissolved in 10 mL MeOH and 10 mL 3N sodium carbonate, and stirred for 12 hours at room temperature. All the solvent was removed, 10 mL or water was added, and the pH was neutralized to 3-4 by 1N HCl. Filtered and dried to give white powder 0.076 g in 81% yield. $R_f$ 0.08 ($CHCl_3/CH_3OH/AcOH$, 10/1/0.5); $^1H$ NMR (DMSO-$d_6$) δ1.94 (m, 1H), 2.09 (m, 1H), 2.35 (m, 1H), 2.80 (d, 3H), 4.31 (d, 2H), 4.57 (m, 1H), 6.02 (s, 2H), 6.03 (d, 1H), 7.55 (d, 2H), 7.98 (d, 2H), 8.70 (d, 1H), 10.23 (br, 1H), 11.01 (br, 1H), 12.35 (br, 2H). anal. ($C_{21}H_{22}N_6O_7$. 0.838$H_2O$) CHN.

Scheme 3. Synthesis of Compound 1c (as shown in FIG. 1c)

2-Amino-4-oxo-4,7-dihydro-3H-pyrrolo[2,3-d]-pyrimidin-6-carboxylic acid (compound 12)

2,6-diamino-4-hydroxy pyrimidine (12.6 g, 100 mmol), ethyl bromopyrvate (20.4 g, 105 mmol), 100 mL DMF, stirred at room temperature for 3 hours. Filtered. The filtered cake was washed with 1000 mL water and dried for 24 hours to give pale powder. The resultant solid was hydrolyzed with 6N NaOH at 60° C. for 3 hours. The reaction mixture was neutralized to pH 1 with 1N HCl. Filtered and dried to afford white powder 17.23 g in 89% yield. $R_f$ 0.05 ($CHCl_3/CH_3OH$, 5/1); $^1H$ NMR (DMSO-$d_6$) δ 6.03 (br, 2H-ex), 8.0 (s, 1H), 10.6 (br, 1H, exchange), 11.2 (br, 1H).

Methyl 4-[4-(2-Amino-4-oxo-4,7-dihydro-3H-pyrrolo[2,3-d]-pyrimidin-6-yl)-carbonylaminomethyl]phenyl-4-carboxylate (compound 13)

Compound 12 (1 mmol), 4-aminomethyl phenylcarboxylate methyl ester (0.173 g, 1.05 mmol) were dissolved in 3 mL DMF. CDI (0.486 g, 3 mmol) was added and stirred for 12 hours at room temperature. All the solvent was removed and directly made silica gel plague. Column separation offered purified white powder 0.265 g compound 13 in 78% yield. $R_f$ 0.45 ($CHCl_3/CH_3OH$, 10/1); $^1H$ NMR (DMSO-$d_6$) δ 3.84 (d, 3H), 4.54 (d, 2H), 6.20 (s, 2H), 7.45 (m, 2H), 7.96 (m, 2H), 8.12 (s, 2H), 9.17 (t, 1H), 11.01 (br, 1H), 12.16 (br, 1H). anal. ($C_{16}H_{15}N_5O_4$. 3.46$H_2O$) CHN.

4-[4-(2-Amino-4-oxo-4,7-dihydro-3H-pyrrolo[2,3-d]-pyrimidin-6-yl)-carbonylaminomethyl]phenyl-4-carboxylate (compound 14)

Compound 13 (0.171 g, 0.5 mmol) was dissolved in 10 mL MeOH and 10 mL 3N sodium carbonate, and stirred for 12 hours at room temperature. All the solvent was removed, 10 mL of water was added and neutralized to a pH of 3-4 by 1N HCl. Filtered and dried to give white powder 0.157 g in 96% yield. $R_f$ 0.40 ($CHCl_3/CH_3OH/AcOH$, 10/1/1); $^1H$ NMR (DMSO-$d_6$) δ 4.50 (d, 2H), 6.02 (s, 2H), 7.48 (m, 2H), 7.95 (m, 2H), 8.06 (s, 1H), 9.16 (br, 1H), 12.4 (br, 3H). anal. ($C_{15}H_{13}N_5O_4$. 0.75$H_2O$) CHN.

2-({4-[4-(2-Amino-4-oxo-4,7-dihydro-3H-pyrrolo[2,3-d]-pyrimidin-6-yl))-carbonylaminomethyl]phenyl-4-carbonyl}amino)pentanedioic dimethyl ester (compound 15)

To a 250 mL round-bottomed flask was added a mixture of compound 14 (0.131 g, 0.4 mmol), N-methylmorpholine (0.081 g, 0.8 mmol), 2-chloro-4,6-dimethoxy-1,3,5-triazine (0.0875 g, 0.5 mmol), and anhydrous DMF (3 mL). The mixture was stirred for 1.5 hours at room temperature. N-methylmorpholine (0.081 g, 0.8 mmol) and L-glutamic acid dimethyl ester hydrochloride (0.105 g, 0.5 mmol) were added to the flask, and the reaction mixture was then stirred at room temperature for 12 hours. After evaporation of solvent under reduced pressure, MeOH (20 mL) was added followed by silica gel (1 g). The resulting plug was loaded onto a silica gel column (2.5 cm×12 cm) and eluted with 10% MeOH in CHCl$_3$. Fractions with the desired Rf (TLC) were pooled and evaporated to give white powder 0.134 g in 69% yield. R$_f$ 0.45 (CHCl$_3$/CH$_3$OH, 10/1); $^1$H NMR (DMSO-d$_6$) δ 1.96 (m, 1H), 2.03 (m, 1H), 2.45 (m, 2H), 3.58 (d, 6H), 4.54 (m, 1H), 4.53 (d, 2H), 6.20 (s, 2H), 7.38 (d, 2H), 7.86 (d, 2H), 8.12 (s, 1H), 8.72 (d, 1H), 9.16 (m, 1H), 11.18 (br, 2H).

2-({4-[4-(2-Amino-4-oxo-4,7-dihydro-3H-pyrrolo[2,3-d]-pyrimidin-6-yl))-carbonylaminomethyl]phenyl-4-carbonyl}amino)pentanedioic acid (compound 1c)

Compound 15 (0.097 g, 0.2 mmol) was dissolved in 10 mL MeOH and 10 mL 3N sodium carbonate, and stirred for 12 hours at room temperature. All the solvent was removed, 10 mL of water was added and neutralized the pH to 3-4 by 1N HCl. Filtered and dried to give white powder 0.072 g in 79% yield. R$_f$ 0.10 (CHCl$_3$/CH$_3$OH/AcOH, 10/1/1); $^1$H NMR (DMSO-d$_6$) δ 1.92 (m, 1H), 2.07 (m, 1H), 2.36 (m, 2H), 4.37 (m, 1H), 4.53 (d, 2H), 6.24 (s, 2H), 7.41 (d, 2H), 7.85 (d, 2H), 8.12 (s, 1H), 8.59 (d, 1H), 9.18 (m, 1H), 12.5 (br, 2H). anal. (C$_{20}$H$_{20}$N$_6$O$_7$ · 0.955H$_2$O) CHN.

We claim:

1. A compound, or pharmaceutically acceptable salt thereof, having a general formula 1:

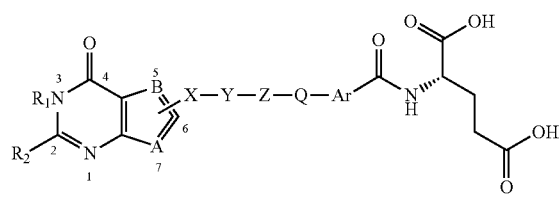

(1)

wherein,
R$_1$ is hydrogen;
R$_2$ is NHR wherein R is hydrogen;
A is NR', wherein R' is hydrogen;
B is CR'R", wherein R' and R" are each hydrogen;
the position of the side chain on the five-membered ring is selected from the group consisting of position 5 and 6;
one X, Y, Z and Q is (CR'R")$_n$, wherein n is 0; and
Ar is monocyclic aryl or heteroaryl ring.

2. The compound of claim 1, or pharmaceutically acceptable salt thereof, selected from a formula 1a, 1b, 1c and 1d:

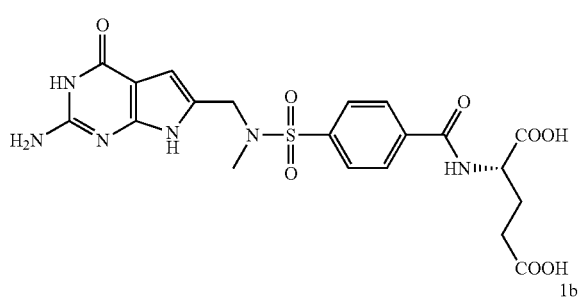

1a

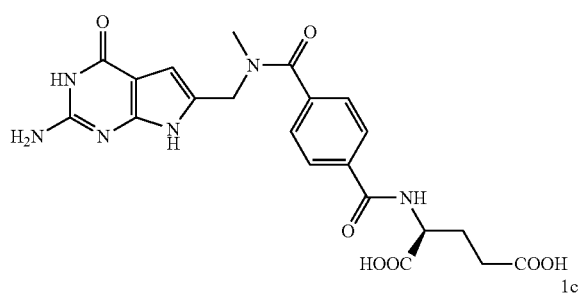

1b

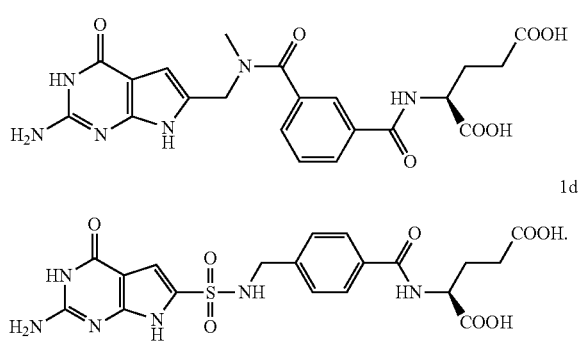

1c

1d

* * * * *